(12) United States Patent
El-Ahmad et al.

(10) Patent No.: US 7,396,934 B2
(45) Date of Patent: Jul. 8, 2008

(54) PROCESS FOR PREPARING 3-FLUOROQUINOLINES

(76) Inventors: Youssef El-Ahmad, 11, avenue de Verdun, F-94000 Creteil (FR); Jean-Pierre Leconte, 17, Avenue Gallieni, F-91800 Brunoy (FR); Joël Malpart, 77, allee Arnoul Greban, F-45160 Olivet (FR); Serge Mignani, 14, avenue de Robinson, F-92290 Chatenay Malabry (FR); Stéphane Mutti, 122, avenue du Maréchal Joffre, F-94170 Le Perreux sur Marne (FR); Michel Tabart, 3, Rue Paul Langevin, F-91290 La Norville (FR)

( * ) Notice: Subject to any disclaimer, the term of this patent is extended or adjusted under 35 U.S.C. 154(b) by 423 days.

(21) Appl. No.: 10/985,533

(22) Filed: Nov. 10, 2004

(65) Prior Publication Data
US 2005/0182259 A1    Aug. 18, 2005

Related U.S. Application Data

(60) Provisional application No. 60/538,368, filed on Jan. 22, 2004.

(30) Foreign Application Priority Data
Nov. 17, 2003  (FR) ................... 03 13384

(51) Int. Cl.
C07D 215/38    (2006.01)
C07D 215/18    (2006.01)
(52) U.S. Cl. ..................... 546/159; 546/180
(58) Field of Classification Search ............ 546/180, 546/159
See application file for complete search history.

(56) References Cited

FOREIGN PATENT DOCUMENTS
WO    WO 2005/049575    6/2005

OTHER PUBLICATIONS

Roe, J Am Chem Soc, vol. 71, pp. 1785-1786, 1949.*
Elderfield, J Am CHem Soc, vol. 68, pp. 1589-1591, 1946.*

Arthur Roe et al., The Preparation of Heterocyclic Fluorine Compounds by the Schiemann Reaction, J. Am. Chem. Soc. (1949, pp. 1785-1786, vol. 71).
International Search Report issued May 13, 2005 in PCT/FR2004/002910 (1 page), with English translation (1 page).
Preliminary International Search Report issued Oct. 7, 2005 in PCT/FR2004/002910 (5 pages), with English translation (4 pages).

* cited by examiner

Primary Examiner—D. Margaret Seaman
(74) Attorney, Agent, or Firm—Harness, Dickey & Pierce, P.L.C.

(57)    ABSTRACT

The invention relates to a novel preparation of 3-fluoroquinolines of formula (I)

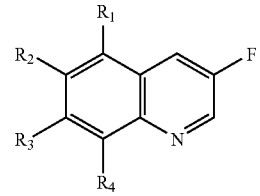

(I)

in which $R_1$, $R_2$, $R_3$ and $R_4$ represent:
  a) a fluorine;
  b) an alkyl optionally substituted with one to three fluorines, with $OR_5$ in which $R_5$ is an alkyl, a hydrogen or a hydroxyl-protecting group, or with NR'R" in which R' and R" represent an alkyl, a hydrogen or an amino-protecting group;
  c) $OR_6$ in which $R_6$ represents a hydrogen, a phenol-protecting group or an alkyl, optionally substituted with a fluorine, with $OR_5$ or with NR'R" as defined above;
  d) $NR'_1R"_1$ in which $R'_1$ and $R"_1$ have the values of R' et R" or represent an alkyl substituted with a fluorine, with $OR_5$ or NR'R" as defined above;
  e) $CO_2R_a$, in which $R_a$ represents hydrogen, alkyl or a carboxyl-protecting group, and also novel intermediate compounds.

The quinolines of formula (I) are intermediates useful in the preparation of compounds having antibacterial activity, described in particular in applications WO 02/40474 or WO 02/72572.

16 Claims, No Drawings

PROCESS FOR PREPARING 3-FLUOROQUINOLINES

This application claims the benefit of U.S. Provisional Application No. 60/538,368, filed Jan. 22, 2004 and benefit of priority of French Patent Application No. 03/13,384, filed Nov. 17, 2003, both of which are incorporated herein by reference in their entirety.

BACKGROUND OF THE INVENTION

Field of the Invention

The invention relates to a process for preparing 3-fluoroquinolines.

SUMMARY OF THE INVENTION

The invention relates to a novel process for preparing 3-fluoroquinolines of general formula (I):

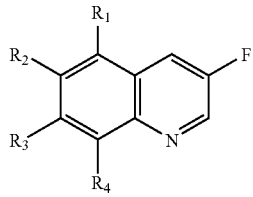

(I)

in which $R_1$, $R_2$, $R_3$ and $R_4$, which may be identical or different, represent:
- a fluorine atom;
- a linear, branched or cyclic alkyl radical optionally substituted with one to three fluorine atoms, with a group $OR_5$ in which $R_5$ represents a linear or branched alkyl radical, a hydrogen atom or a hydroxyl radical-protecting group, or with a group NR'R" in which R' and R", which may identical or different, represent a linear or branched alkyl radical, a hydrogen atom or an amino radical-protecting group;
- a group $OR_6$ in which $R_6$ represents a hydrogen atom, a phenol-protecting group or a linear or branched alkyl radical optionally substituted with one to three fluorine atoms, with $OR_5$ or with NR'R" as defined above;
- a group $NR'_1R''_1$ in which $R'_1$ and $R''_1$ have the values of R' and R" or represent a linear or branched alkyl radical substituted with one to three fluorine atoms, with a group $OR_5$ as defined above or with a group NR'R" as defined above;
- a group $CO_2R_a$, in which $R_a$ represents a hydrogen atom, a linear or branched alkyl radical or a carboxyl radical-protecting group;
- a phenyl radical or a heteroaryl radical, optionally substituted with one or more of the substituents mentioned above.

DETAILED DESCRIPTION OF THE INVENTION

In the general formula above, it is understood that the alkyl radicals contain 1 to 10 carbon atoms in a linear or branched chain and that the cycloalkyl radicals contain 3 to 6 carbon atoms.

When the compounds bear a heteroaryl substituent, the latter contains 5 to 10 ring members and may be monocyclic or bicyclic and chosen (in a nonlimiting manner), from thienyl, furyl, pyrrolyl, imidazolyl, thiazolyl, oxazolyl, thiadiazolyl, oxadiazolyl, tetrazolyl, pyridyl, pyridazinyl, pyrazinyl, pyrimidinyl, indolyl, benzothienyl, benzofuranyl, indazolyl, benzothiazolyl, naphthyridinyl, quinolyl, isoquinolyl, cinnolyl, quinazolyl, quinoxalyl, benzoxazolyl and benzimidazolyl, which may be optionally substituted with the substituents stated above.

According to the invention, the products of general formula (I) are obtained by a process wherein a compound of general formula (IV)

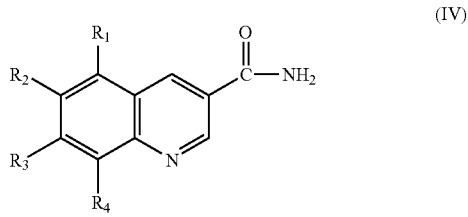

(IV)

in which $R_1$, $R_2$, $R_3$ and $R_4$ are as defined hereinabove, is subjected to a Hofmann degradation, so as to obtain a compound of general formula (III)

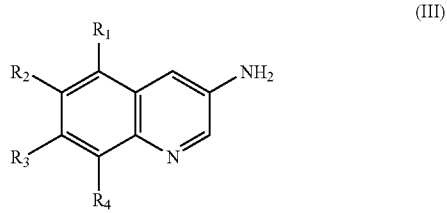

(III)

in which $R_1$, $R_2$, $R_3$ and $R_4$ are as defined hereinabove, which is treated under conditions capable of forming the diazonium salt of general formula (II)

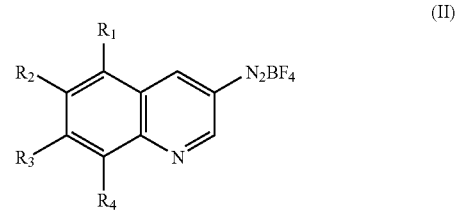

(II)

in which $R_1$, $R_2$, $R_3$ and $R_4$ are as defined hereinabove, which is heated in an inert organic solvent to a temperature of between 35 and 120° C.

The Hofmann degradation is carried out with bromine and sodium hydroxide, and also pyridine, in water, at a temperature of approximately 60° C.

The conditions for preparing the diazonium salt consist, for example, in carrying out the process in the presence of an alkali metal salt or of an ester of nitrous acid, in particular of sodium nitrite or of potassium nitrite or of tert-butyl or isobutyl nitrite, and of fluoroboric acid, or in the presence of boron trifluoride-ethyl ether complex, in an appropriate solvent, in particular THF, water or an alcohol, at a temperature between +15 and +20° C.

In order to convert the compound of formula (II) to a compound of formula (I), the process is preferably carried out in a solvent such as toluene, xylene, heptane, hexane, a fluorinated solvent such as perfluorohexane, or else a chlorinated solvent such as mono- or dichlorobenzene, chlorobutane or methylene chloride.

The above reaction is generally carried out at elevated temperatures and is preferably between about 60 and about 100° C. and depends, of course, on the solvent used.

A subject of the invention is also a process according to the above, wherein the compound of general formula (IV) is obtained by subjecting a compound of formula (V)

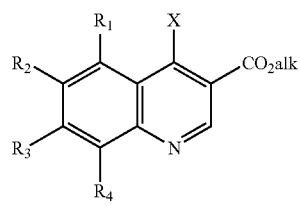

(V)

in which $R_1$, $R_2$, $R_3$ and $R_4$ are as defined hereinabove, X represents a chlorine atom or a bromine atom and alk represents an alkyl radical containing from 1 to 6 carbon atoms, to the action of a hydrogenolysis agent, and then to that of aqueous ammonia, so as to obtain successively the compound of formula (VI)

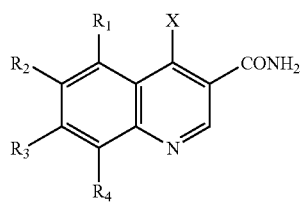

(VI)

which may or may not be isolated, and then the compound of formula (IV).

According to the invention, the two reactions above may be carried out in the reverse order, the compound intermediately formed, and which may or may not be isolated, then being the compound of formula (VII)

(VII)

The hydrogenolysis reaction is carried out in an alcohol, in particular ethanol or methanol, in the presence of triethylamine and of a catalyst such as palladium-on-charcoal, by sparging hydrogen into the reaction medium.

It is also possible to carry out the process in dimethylformamide, in the presence of sodium formate and of tetrakis(triphenylphosphine)palladium.

A subject of the invention is also a process according to the above, wherein the compound of formula (V) is obtained by subjecting a compound of formula (VIII)

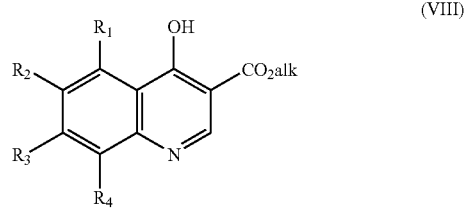

(VIII)

in which $R_1$, $R_2$, $R_3$ and $R_4$ and alk are as defined hereinabove, to the action of phosphorus oxychloride or phosphorus oxybromide.

The process is preferably carried out without a solvent, at a temperature in the order of about 100° C.

A subject of the invention is also a process according to the above, wherein the compound of formula (IV) is obtained by treating a compound of formula (VIII), as defined above, with a base, so as to obtain a corresponding acid of formula (IX)

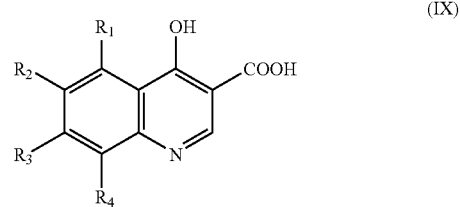

(IX)

in which $R_1$, $R_2$, $R_3$ and $R_4$ are as defined hereinabove, which is subjected to the action of phosphorus oxychloride or of phosphorus oxybromide, so as to obtain a compound of formula (X)

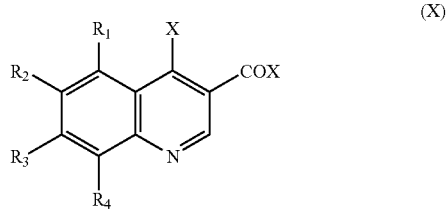

(X)

in which $R_1$, $R_2$, $R_3$, $R_4$ and X are as defined hereinabove, which is subjected to the action of ammonia so as to obtain a compound of formula (VII) as defined above, which is subjected to the action of a hydrogenolysis agent.

The saponification reaction is carried out under conventional conditions known to those skilled in the art, in particular by the action of sodium hydroxide or potassium hydroxide in aqueous medium at reflux temperature.

The action of the phosphorus oxychloride or the phosphorus oxybromide is preferably carried out at the reflux temperature thereof, without solvent.

The hydrogenolysis agent is one of those which were mentioned above.

A subject of the invention is also a process according to the above, wherein the compound of formula (IV) is obtained by heating a compound of formula (XI)

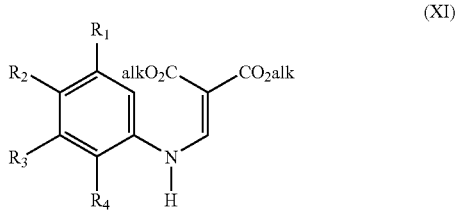

in which $R_1$, $R_2$, $R_3$, $R_4$ and alk are as defined hereinabove, in the presence of phosphorus pentoxide, so as to obtain a compound of formula (IX) as defined above, and then pursuing the synthesis as described above.

The reaction of the phosphorus pentoxide with the compound of formula (XI) is preferably carried out in a solvent such as nitrobenzene at a temperature in the order of about 120-130° C.

The compound of formula (V) may also be obtained by subjecting a compound of formula (XI) as defined above to the action of phosphorus oxychloride or of phosphorus oxybromide.

The process is preferably carried out without solvent, at a temperature in the order of about 100° C., starting with a compound of formula (XI) in which the sensitive groups on $R_1$, $R_2$, $R_3$ and $R_4$ are pre-protected.

The compound of formula (VIII) may be obtained by heating a compound of formula (XI) as defined above, in a solvent with a high boiling point.

The cyclization of the compound of formula (XI) is preferably carried out in diphenyl ether, at reflux temperature or at a temperature similar to the reflux of the latter.

The compound of general formula (XI) is obtained by reacting a compound of general formula (XII)

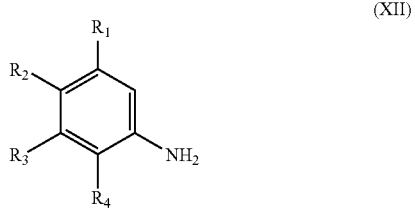

in which $R_1$, $R_2$, $R_3$ and $R_4$ are as defined hereinabove, with a compound of general formula (XIII)

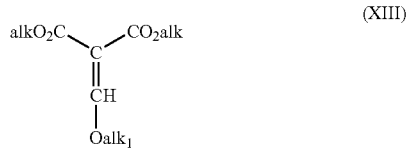

in which alk is as defined hereinabove and $alk_1$ represents a linear or branched alkyl radical which may be identical or different to alk.

Under preferential conditions, the reaction is carried out without the addition of a solvent, by heating to a temperature of from about 80 to about 120° C.

According to the definitions of $R_1$, $R_2$, $R_3$ and $R_4$, it may be desirable, or even necessary, depending on the type of reaction involved, to use compounds in which the substituents are protected. These are in particular the alkyl substituents substituted with $OR_5$ or with NR'R'', $OR_6$, $NR'_1R''_1$ and $CO_2R_a$.

A subject of the invention is in particular a process as defined above, wherein use is made of compounds in which the possible sensitive substituents are protected, during the preparation of the compounds of formula (X) from the compounds of formula (IX) and also during the Hofmann degradation producing the compounds of formula (III) from the compounds of formula (IV). According to the invention, the compounds involved are either protected from the beginning of synthesis or just before the critical step is carried out.

The protective groups which may be used and also the use thereof are known to those skilled in the art and described, for example, by T. W. Greene and P. G. M. Nuts, "Protective Groups in Organic Synthesis" (John Wiley & Sons, inc.).

A subject of the invention is in particular a process according to the above, wherein use is made of compounds in which $R_1$, $R_2$, $R_3$ and $R_4$, which may be identical or different, represent a hydrogen atom, a fluorine atom, an optionally substituted linear or branched alkyl radical as defined above, or a radical $OR_6$ as defined above.

The subject of the invention is more particularly a process wherein use is made of compounds in which $R_1$, $R_2$, $R_3$ and $R_4$, which may be identical or different, represent a hydrogen atom, a fluorine atom or a radical $OR_6$ as defined above, and in particular an alkoxy radical.

Finally, a subject of the invention is a compound of formula (II) as defined above.

The compounds of formula (I) are intermediate compounds useful in particular in the preparation of compounds having antibacterial activity, described, for example, in applications WO 02/72572 and WO 02/40474.

This invention is further illustrated by the following examples which are provided for illustration purposes and in no way limit the scope of the present invention.

EXAMPLES

Example 1

Preparation of 3-fluoro-6-methoxyquinoline

A suspension of 1007 g of 6-methoxy-3-quinolinediazonium fluoroborate taken in 9 l of toluene is heated to 60° C. in 85 minutes. A release of gas is observed at 60° C. The reaction medium is then gradually heated further for 90 minutes to 70-72° C. After having been kept at 72° C. for 90 minutes, the medium is then gradually heated again to 85° C. After cooling and stirring overnight, 4 l of ice-cold water are added to the suspension. After having stirred for 15 minutes, 2.5 l of ethyl acetate are added. After having stirred for 45 minutes, the pH is adjusted to pH=7-7.5 by adding 47% sodium hydroxide (250 ml). The medium is stirred for 30 minutes and then separated by settling out for 1 hour. The lower aqueous phase is re-extracted with ethyl acetate. The organic phases are combined together and washed with water. The solution is filtered and then concentrated under reduced pressure so as to give 655 g of crude 3-fluoro-6-methoxyquinoline. The crude product is distilled under reduced pressure. The distillation fractions (bp 103-110° C. under 1 mbar) containing the expected product are combined together. 498.9 g of 3-fluoro- 6-methoxyquinoline (76%) are thus obtained in the form of a white solid which melts at 51-53° C.

Microanalysis: $C_{10}H_8FNO$ calculated C 67.79; H 4.55; F 10.72; N 7.91; O 9.03 found C 67.98; H 4.54; N 7.97

NMR spectrum: $^1H$ (300 MHz, $(CD_3)_2SO$ d6, δ in ppm): 3.92 (s: 3H); 7.40 (mt: 2H); 7.97 (d, J=10 Hz: 1H); 8.13 (dd, J=10 and 3 Hz: 1H); 8.76 (d, J=3 Hz: 1H).

Mass spectrum:

| m = 177 | | |
|---|---|---|
| EI | m/z = 177 | $M^{+\cdot}$ base peak |
|  | m/z = 134 | $[M - COCH_3]^{+\cdot}$ |
| DCI | m/z = 178 | $MH^+$ base peak |

3-Diazoniumfluoroborate-6-methoxyquinoline

3-Amino-6-methoxyquinoline (10 g) are suspended in 50 ml of THF and stirred for 15 minutes at 20° C., before being cooled to −15° C. 11.6 g of $BF_3$-etherate are then added. The temperature of the reaction mass is brought to −15° C. After 15 minutes at this temperature, 7.5 g of tert-butyl nitrite at 90% in solution in 25 ml of THF are added over 10 minutes. The suspension is stirred for 1 hour at −15° C., before being brought to +15° C. over a period of one hour. The precipitate is filtered off, washed with hexane and then dried at 15-20° C. under constant pressure until a constant weight is obtained. 14.8 g (94.3%) of 3-diazoniumfluoroborate-6-methoxyquinoline are obtained in the form of a yellow solid. Decomposition temperature: 82° C.

3-Amino-6-methoxyquinoline 104 kg of a 32% sodium hydroxide solution are added to 341 kg of water. The solution is cooled to 0° C. and 22.0 kg of bromine are introduced over 1.5 hours while maintaining the temperature at 0° C. The solution is stirred at this temperature for 1 hour, and then 409 kg of pyridine are introduced over 3 hours at 0° C. 26.5 kg of 6-methoxy-quinoline-3-carboxamide are then added over 50 minutes at 0° C. The reaction medium is kept at this temperature for 2 hours and then gradually heated to 60° C. over 1 hour. After maintaining the temperature at 60° C. for 6 hours, the reaction mass is cooled to 20° C. and separated by settling out. The aqueous phase (172 kg) is washed with pyridine (60 liters). The organic phases are pooled (820 kg) and concentrated to dryness under reduced pressure (100-150 mbar) at a maximum of 84° C. The residue is then taken up with 425 l of water and 43 l of ethanol. The suspension obtained is refluxed for 1 hour and then cooled. The product begins to precipitate at a temperature of 65° C. The medium is then cooled to 0-5° C., and kept at this temperature for 2 hours. The precipitate is filtered off, washed with cold water, and then dried at 50-55° C. under reduced pressure. 16.5 kg (72.3%) of 3-amino-6-methoxyquinoline are obtained in the form of a brown solid (HPLC titer=99.1%), having a melting point of 108-110° C. A second crop of 3.7 kg (13.1%) is obtained from the mother liquors (HPLC titer=98%).

NMR spectrum: $^1H$ (300 MHz, $(CD_3)_2SO$ d6, δ in ppm): 3.84 (s: 3H); 5.65 (s: 2H); 6.97 (dd, J=9 and 3 Hz: 1H); 7.01 (d, J=3 Hz: 1H); 7.08 (d, J=2.5 Hz: 1H); 7.67 (d, J=9 Hz: 1H); 8.29 (d, J=2.5 Hz: 1H).

IR spectrum: (KBr) 3454; 3312; 3204; 1630; 1619; 1607; 1504; 1383; 1251; 1239; 1216; 1167; 1027; 872; 827; 627 and 479 $cm^{-1}$ Mass spectrum: m=174 EI m/z=174 ($M^+$)–base peak m/z=131 $[M-COCH_3]^+$.

6-Methoxyquinoline-3-carboxamide 380 l of ethanol are added to 49.2 kg of 4-chloro-3-ethoxycarbonyl-6-methoxyquinoline. The suspension is heated at 45° C. for 30 minutes and then cooled to 20° C. 18.65 kg of triethylamine are added under nitrogen, followed by 1.91 kg of palladium-on-charcoal at 5% (at 60% water content). A stream of hydrogen is passed through under 0.5-0.8 bar at 33° C. for 48 hours. At this time, an $HPLC^1$ control shows that the reaction is complete. The reactor is then vented with nitrogen and the reaction medium is then filtered to remove the catalyst. The filter is then rinsed with ethanol. The filtrate is poured over 750 kg of an aqueous ammonia solution. The reaction medium is then stirred at 25° C. over a period of 4 days. The ethanol is then removed by distillation under reduced pressure at a temperature not exceeding 40-45° C. The suspension thus obtained is cooled to 0-5° C. and stirred for 3 hours at this temperature. The precipitate is filtered off, washed with cold water, and then dried at 60-65° C. under reduced pressure until a constant weight is obtained. 26.5 kg (71%) of 6-methoxyquinoline-3-carboxamide are obtained in the form of a white solid which melts at 93.7-95.7° C. ($HPLC_{\%NIS}=98.3\%$).

NMR spectrum: $^1H$ (300 MHz, $(CD_3)_2SO$ d6, δ in ppm): 3.94 (s: 3H); 7.45 (d, J=3 Hz: 1H); 7.52 (dd, J=9 and 3 Hz: 1H); 7.67 (broad s: 1H); 8.00 (d, J=9 Hz: 1H); 8.29 (broad s: 1H); 8.74 (d, J=2 Hz: 1H); 9.15 (d, J=2 Hz: 1H).

IR spectrum: (KBr) 3408; 3330; 3211; 1697; 1626; 1511; 1386; 1321; 1240; 1023; 935; 826 and 693 $cm^{-1}$ Mass spectrum:

| m = 202 | | |
|---|---|---|
| EI | m/z = 202 | $[M^+]$ – base peak |
| m/z = 186 | $[M - NH_2]^+$ | |
| m/z = 158 | $[186 - CO]^+$ | |

4-Chloro-3-ethoxycarbonyl-6-methoxyquinoline 132 g of phosphoryl chloride are added, at 25° C., to 50 g of diethyl 2-[(4-methoxyphenylamino)methylene]malonate. The reaction medium is stirred for 15 minutes at this temperature, heated to 95-100° C. over 45 minutes, and then kept at this temperature for 4 hours. The excess phosphoryl chloride is then removed by heating at 125° C. for approximately 2 hours. The mixture is then cooled to 25° C. and 125 ml of dichloromethane are added. The medium is then stirred at 25° C. for 1 hour, and then run into 900 ml of water, over 30 minutes, while maintaining the temperature below 30° C. The pH is then adjusted to 7.5-8 by adding 172 g of a 47% sodium hydroxide solution, while maintaining the temperature at 20-25° C. The 2 phases are separated and the aqueous phase is extracted with dichloromethane. The organic phases are pooled and washed with water. The dichloromethane phase is half-concentrated and 190 ml of ethanol are added. The concentration is continued until the temperature of the reaction mass reaches 82° C. and the vapor temperature reaches 78° C. The reaction mass is cooled to 0-5° C. and then kept at this temperature for 2 hours. The precipitate is filtered off, washed with cold ethanol, and then dried at 50° C. under reduced pressure. 27.7 g (61%) of 4-chloro-3-ethoxycarbonyl-6-methoxyquinoline are obtained in the form of a yellow solid which melts at 93.7-95.7° C.

Titer (HPLC.): 98.0%

Diethyl
2-[(4-methoxyphenylamino)methylene]malonate 3.5 kg of p-anisidine are added to 6.25 kg of diethyl ethoxymethylenemalonate at 14° C., over 85 minutes without cooling of the reaction mass. At the end of addition, the temperature has reached 59° C. The temperature is kept at 59° C. for 30 minutes, and the reaction medium is then heated to 90-95° C. and kept at this temperature for 1 hour. The ethanol formed is then removed by distillation at atmospheric pressure and then under 250 mbar. After cooling to 45° C., 8.4 kg of diethyl 2-[(4-methoxyphenylamino)methylene]malonate are recovered in the form of a brown viscous oil, with a quantitative yield.

Titer (HPLC.): 98.3%

REFERENCES

1/Description of the analytical conditions:

| Method: | HPLC |
|---|---|
| Column: | Hichrom 100 RP18 5µ (250 × 4.6 mm) |
| Flow rate: | 1 ml/min |
| Wavelength: | 210 nm |
| Injection volume: | 20 µl |
| Eluent: | 400 ml acetonitrile |
| | 600 ml 0.01 M sodium dihydrogen phosphate (pH 2.3) |
| | 2.88 g/l sodium dodecyl sulfate. |
| Injection: | 20 µl of 0.1 mg/ml solution. |

Retention Time:

| p-anisidine | 12.16 min |
|---|---|
| 2-[(4-methoxyphenylamino)methylene]malonic acid diethyl ester | 25.0 min |
| 3-ethoxycarbonyl-6-methoxy-4(1H)-quinolinone | 4.15 min |
| 4-chloro-6-methoxyquinoline-3-ethyl carboxylate | 24.1 min |
| 6-methoxyquinoline-3-ethyl carboxylate | 16.5 min |
| 6-methoxyquinoline-3-carboxamide | 6.0 min |
| 3-amino-6-methoxyquinoline | 16.2 min |
| 3-fluoro-6-methoxyquinoline | 10.0 min |

Example 2

3,7-Difluoro-6-methoxyquinoline 6.1 g of 3-amino-7-fluoro-6-methoxyquinoline are added, with stirring at a temperature in the region of −5° C., to an aqueous 40% fluoroboric acid solution, and a solution of 2.6 g of sodium nitrite in 5.2 cm³ of water is then added over 20 minutes. The reaction mixture is stirred at a temperature in the region of +3° C. for 40 minutes, and then filtered. The solid is washed with an aqueous 40% fluoroboric acid solution at −5° C., then with a mixture of isopropanol and of an aqueous 40% fluoroboric acid solution at −5° C., and then with ethyl ether, spin-filtered to dryness and dried under reduced pressure. 9.95 g of a solid are thus obtained, which are dissolved in 80 cm³ of anhydrous toluene, and this solution is brought to 92° C. for 1 hour with vigorous stirring. After cooling to ambient temperature, 50 cm³ of toluene are added, followed by 80 cm³ of a saturated aqueous solution of sodium hydrogen carbonate. The reaction medium is separated by settling out, the aqueous phase is extracted with toluene, and the organic phases are pooled, washed with a saturated aqueous solution of sodium chloride, and then dried over sodium sulfate. After filtration and then evaporation to dryness under reduced pressure of the toluene, the residue is chromatographed on a silica column (100 g, particle size 20-46 µm, eluent: dichloromethane). The fractions containing the expected product are evaporated to dryness under reduced pressure. 2.28 g of 3,7-difluoro-6-methoxyquinoline are obtained, in the form of a white solid which melts at 98° C.

3-Amino-7-fluoro-6-methoxyquinoline 2.4 cm³ of bromine are added dropwise, over 30 minutes, to a solution of 133 cm³ of aqueous 2N sodium hydroxide solution cooled to 0° C., followed by 111 cm³ of pyridine. 10.1 g of 7-fluoro-6-methoxyquinoline-3-carboxamide are then added to this solution, still at 0° C., and the mixture is stirred at 0° C. for 2 hours 30 min. The reaction medium is then allowed to warm back up to ambient temperature, and is then heated with stirring to 60° C. for 18 h. It is then allowed to cool down again to ambient temperature, and 100 cm³ of water, followed by 100 cm³ of ethyl acetate, are then added. The reaction medium is separated by settling out, the aqueous phase is extracted with ethyl acetate, and the aqueous phases are pooled, washed with water and then dried over sodium sulfate and evaporated to dryness under reduced pressure. 8.25 g of a solid residue are obtained, which residue is triturated in 150 cm³ of isopropyl ether and filtered. The solid is washed with isopropyl ether and then with pentane. After drying, 6.20 g of 3-amino-7-fluoro-6-methoxyquinoline are obtained, in the form of a light brown solid which melts at 153° C.

7-Fluoro-6-methoxyquinoline-3-carboxamide 5.58 g of sodium formate and 3.16 g of tetrakis(triphenylphosphine)palladium are added to a solution of 13.9 g of 4-chloro-7-fluoro-6-methoxyquinoline-3-carboxamide in 278 cm³ of dimethylformamide, and this solution is heated under an argon atmosphere at 100° C. for 5 hours. After cooling to ambient temperature, the reaction medium is filtered. The filtrate is concentrated under reduced pressure so as to obtain 200 cm³ of a solution, to which 600 cm³ of water are added. The precipitate formed is filtered off, washed with water and then dried at 50° C. under reduced pressure. The solid obtained is washed with toluene, then twice with ethyl ether, and then with pentane. 10.7 g of 7-fluoro-6-methoxyquinoline-3-carboxamide are obtained, in the form of a beige solid which melts at 231° C.

4-Chloro-7-fluoro-6-methoxyquinoline-3-carboxamide

A stirred solution of 15.83 g of 7-fluoro-4-hydroxy-6-methoxyquinoline-3-carboxylic acid in 40 cm³ of phosphoryl chloride is brought to 100° C. for 3 hours. After cooling to ambient temperature, the reaction medium is distilled under atmospheric pressure in order to remove the phosphoryl chloride. The residue is dissolved in 70 cm³ of dichloromethane, and then ammonia is sparged into this solution, which is kept at 25° C. with stirring for 5 hours. The reaction medium is then filtered, and the solid obtained is washed with dichloromethane and then dried at 50° C. under reduced pressure.

14.05 g of 4-chloro-7-fluoro-6-methoxy-quinoline-3-carboxamide are obtained, in the form of an off-white solid which melts at 228° C.

7-Fluoro-4-hydroxy-6-methoxyquinoline-3-carboxylic acid

A stirred solution of 23.57 g of ethyl 7-fluoro-4-hydroxy-6-methoxyquinoline-3-carboxylate in 71 cm³ of an aqueous 5N sodium hydroxide solution is brought to 100° C. for 3 hours. After cooling to ambient temperature, the reaction medium is acidified by adding 32.5 cm³ of an aqueous 37% hydrochloric acid solution. After addition of 150 cm³ of water, the precipitate obtained is filtered off and the solid is washed with water. After drying in the open air, 22 g of 7-fluoro-4-hydroxy-6-methoxyquinoline-3-carboxylic acid are obtained, in the form of a cream solid which melts at 275° C.

Ethyl 7-fluoro-4-hydroxy-6-methoxyquinoline-3-carboxylate

A stirred solution of 37.75 g of diethyl 2-[(3-fluoro-4-methoxyphenylamino)methylene]malonate in 170 cm³ of diphenyl ether is brought to 245° C. for 3.5 hours. After cooling to ambient temperature, 220 cm³ of cyclohexane are added, and the precipitate thus obtained is filtered off and washed with cyclohexane and then with pentane and is spin-filtered to dryness. 24.10 g of ethyl 7-fluoro-4-hydroxy-6-methoxy-quinoline-3-carboxylate are obtained, in the form of a solid which melts at 280° C.

Diethyl 2-[(3-fluoro-4-methoxyphenylamino)methylene]malonate

A stirred mixture of 15.61 g of 3-fluoro-4-methoxyaniline and of 24.25 g of diethyl ethoxymethylenemalonate is brought to 100° C. for 2.5 hours. After cooling to ambient temperature and then evaporation to dryness at 50° C. under reduced pressure, 35 g of diethyl 2-[(3-fluoro-4-methoxyphenylamino)methylene]malonate are obtained, in the form of a beige solid which melts at 63° C.

Example 3

3,8-Difluoro-6-methoxyquinoline

By carrying out the process as described in Example 2, but using 2.35 g of 3-amino-8-fluoro-6-methoxyquinoline, 1.35 g of 3,8-difluoro-6-methoxyquinoline are obtained, in the form of a white solid which melts at 122° C.

Characteristics of the synthesis intermediates:
3-Amino-8-fluoro-6-methoxyquinoline: brown solid which melts at 135° C.
8-Fluoro-6-methoxyquinoline-3-carboxamide: beige solid which melts at 248° C.
4-Chloro-8-fluoro-6-methoxyquinoline-3-carboxamide: light brown solid which melts at 220° C.
8-Fluoro-4-hydroxy-6-methoxyquinoline-3-carboxylic acid: beige solid which melts at around 280° C.
Ethyl 8-fluoro-4-hydroxy-6-methoxyquinoline-3-carboxylate: light brown solid which melts at 221° C.
Diethyl 2-[(2-fluoro-4-methoxyphenylamino)methylene]malonate: mass spectrum EI m/z=311 (M⁺).
2-Fluoro-4-methoxyaniline is used at the start.

Example 4

3,6-Difluoroquinoline

By carrying out the process as described in Example 2, but using 3-amino-6-fluoroquinoline, 3,6-difluoroquinoline is obtained, mass spectrum EI m/z=165 (M⁺).

Characteristics of the synthesis intermediates:
3-Amino-6-fluoroquinoline: mass spectrum EI m/z=162 (M⁺).
6-Fluoroquinoline-3-carboxamide: mass spectrum EI m/z=190 (M⁺).
4-Chloro-6-fluoroquinoline-3-carboxamide: mass spectrum EI m/z=224 (M⁺).
4-Hydroxy-6-fluoroquinoline-3-carboxylic acid: mass spectrum EI m/z=207 (M⁺).
Ethyl 4-hydroxy-6-fluoroquinoline-3-carboxylate: mass spectrum EI m/z=235 (M⁺).
Diethyl 2-[(2-fluoro-4-methoxyphenylamino)methylene]malonate: mass spectrum EI m/z=281 (M⁺).
4-Fluoroaniline is used at the start.

What is claimed is:
1. A process for preparing 3-fluoroquinolines of formula (I):

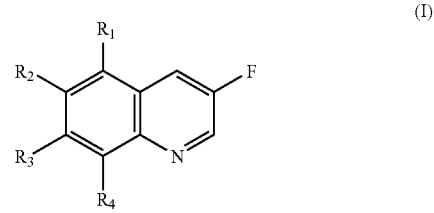

wherein $R_1$, $R_2$, $R_3$ and $R_4$, which may be identical or different, represent:
a hydrogen atom;
a fluorine atom;
a linear, branched or cyclic alkyl radical optionally substituted with one to three fluorine atoms, with a group $OR_5$ in which $R_5$ represents a linear or branched alkyl radical, a hydrogen atom or a hydroxyl radical-protecting group, or with a group NR'R" in which R' and R", which may identical or different, represent a linear or branched alkyl radical, a hydrogen atom or an amino radical-protecting group;
a group $OR_6$ in which $R_6$ represents a hydrogen atom, a phenol-protecting group or a linear or branched alkyl radical optionally substituted with one to three fluorine atoms, with $OR_5$ or with NR'R" as defined above;
a group $NR'_1R''_1$ in which $R'_1$ and $R''_1$ have the values of R' and R" or represent a linear or branched alkyl radical substituted with one to three fluorine atoms, with a group $OR_5$ as defined above or with a group NR'R" as defined above;
a group $CO_2R_a$, in which $R_a$ represents a hydrogen atom, a linear or branched alkyl radical or a carboxyl radical-protecting group;
a phenyl radical or a heteroaryl radical, optionally substituted with one or more of the substituents mentioned above, said process comprising:

a) subjecting a compound of formula (IV):

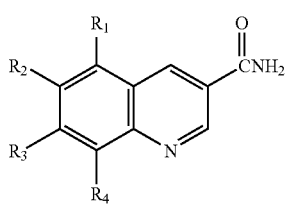
(IV)

wherein $R_1$, $R_2$, $R_3$ and $R_4$ are as defined above, to a Hofmann degradation, so as to obtain a compound of general formula (III):

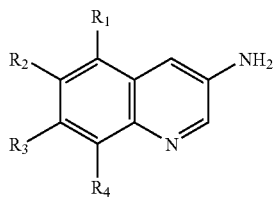
(III)

wherein $R_1$, $R_2$, $R_3$ and $R_4$ are as defined above;

b) treating said compound of formula (III) under conditions capable of forming the diazonium salt of general formula (II):

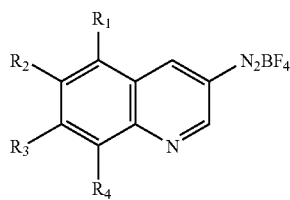
(II)

wherein $R_1$, $R_2$, $R_3$ and $R_4$ are as defined above; and c) heating said compound of formula (II) in an inert organic solvent to form the compound of formula (I).

2. The process as set forth in claim 1, wherein the diazonium salt is prepared by the action of an alkali metal salt or of an alkyl ester of nitrous acid and of fluoroboric acid or of the boron trifluoride-ethyl ether complex.

3. The process as set forth in claim 1, wherein the compound of formula (IV) is obtained by subjecting a compound of formula (V):

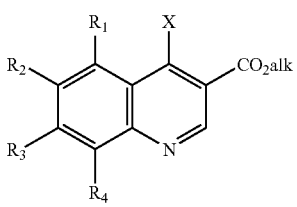
(V)

wherein $R_1$, $R_2$, $R_3$ and $R_4$ are defined as in claim 1, X represents a chlorine atom or a bromine atom and alk represents an alkyl radical containing from 1 to 6 carbon atoms, to the action of a hydrogenolysis agent, to obtain the compound of formula (VI):

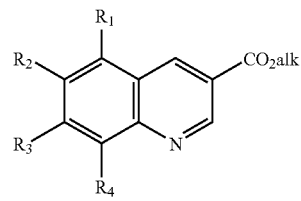
(VI)

treating the compound of formula (VI) with aqueous ammonia to obtain the compound of formula (IV).

4. The process as set forth in claim 3, wherein the compound of formula (VI) is not isolated, and the compound of formula (V) is subjected successively to hydrogenolysis and then treated with ammonia to form directly the compound of formula (IV).

5. The process as set forth in claim 3, wherein the compound of formula (VI) is first isolated and then converted to compound of formula (IV) by the action of aqueous ammonia.

6. The process as set forth in claim 1, wherein the compound of formula (IV) is obtained by subjecting a compound of formula (V):

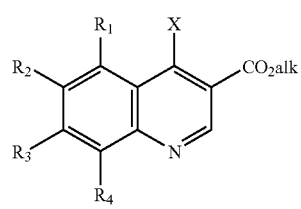
(V)

wherein $R_1$, $R_2$, $R_3$ and $R_4$ are defined as in claim 1, X represents a chlorine atom or a bromine atom and alk represents an alkyl radical containing from 1 to 6 carbon atoms, to the action of aqueous ammonia, so as to obtain a compound of formula (VII):

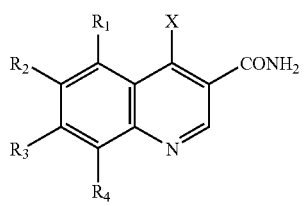
(VII)

wherein $R_1$, $R_2$, $R_3$ and $R_4$ are as defined in claim 1 and X represents a chlorine atom or a bromine atom, which is subjected to the action of a hydrogenolysis agent so as to obtain the compound of formula (IV).

7. The process set forth in claim 3, wherein the compound of formula (V) is obtained by subjecting a compound of formula (VIII):

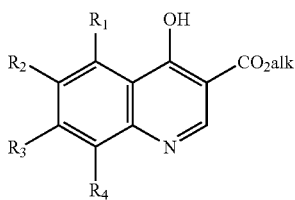

wherein $R_1$, $R_2$, $R_3$ and $R_4$ defined in claim 1 and alk represents an alkyl radical containing from 1 to 6 carbon atoms, to the action of phosphorus oxychloride or phosphorus oxybromide.

8. The process set forth in claim 6, wherein the compound of formula (V) is obtained by subjecting a compound of formula (VIII):

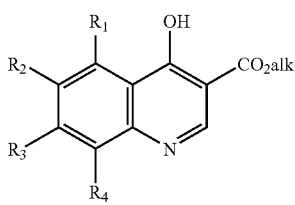

wherein $R_1$, $R_2$, $R_3$ and $R_4$ are as defined in claim 1 and alk represents an alkyl radical containing from 1 to 6 carbon atoms, to the action of phosphorus oxychloride or phosphorus oxybromide.

9. The process as set forth in claim 1, wherein the compound of formula (IV) is obtained by treating a compound of formula (VIII):

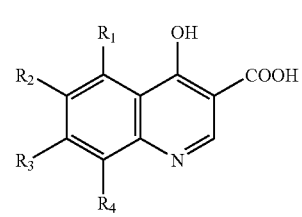

wherein $R_1$, $R_2$, $R_3$ and $R_4$ are as defined in claim 1 and alk represents an alkyl radical containing from 1 to 6 carbon atoms, with a base, so as to obtain a corresponding carboxylic acid of formula (IX):

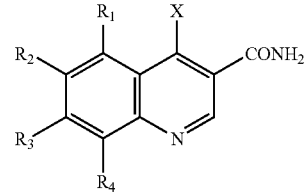

wherein $R_1$, $R_2$, $R_3$ and $R_4$ are as defined in claim 1, which is subjected to the action of phosphorus oxychloride or of phosphorus oxybromide, so as to obtain a compound of formula (X):

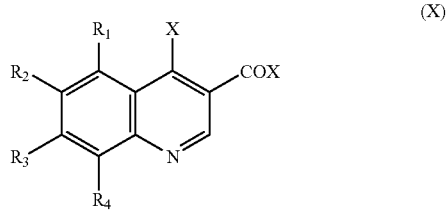

wherein $R_1$, $R_2$, $R_3$ and $R_4$ are as defined in claim 1 and X represents a chlorine atom or a bromine atom, which is subjected to the action of ammonia so as to obtain a compound of formula (VII):

wherein $R_1$, $R_2$, $R_3$ and $R_4$ are as defined in claim 1 and X represents a chlorine atom or a bromine atom, which is subjected to the action of a hydrogenolysis agent to obtain the compound of formula (IV).

10. The process as set forth in claim 1, wherein optionally all of the sensitive substituents in the compound of formula (IV) are suitably protected.

11. The process as set forth in claim 9, wherein optionally all of the sensitive substituents in the compound of formula (IX) are suitably protected.

12. The process as set forth in claim 1, wherein $R_1$, $R_2$, $R_3$ and $R_4$, which may be identical or different, represent a hydrogen atom or a fluorine atom, an optionally substituted linear or branched alkyl radical as defined in claim 1, or a radical $OR_6$ as defined in claim 1.

13. The process as set forth in claim 9, wherein $R_1$, $R_2$, $R_3$ and $R_4$, which may be identical or different, represent a hydrogen atom or a fluorine atom, an optionally substituted linear or branched alkyl radical as defined in claim 1, hydrogen as defined in claim 1, or a radical $OR_6$ as defined in claim 1.

14. The process as set forth in claim 12, wherein $R_1$, $R_2$, $R_3$ and $R_4$, which may be identical or different, represent a hydrogen atom or a fluorine atom, hydrogen, or a linear or branched alkoxy radical containing from 1 to 10 carbon atoms.

15. The process as set forth in claim 13, wherein $R_1$, $R_2$, $R_3$ and $R_4$, which may be identical or different, represent a hydrogen atom or a fluorine atom, hydrogen, or a linear or branched alkoxy radical containing from 1 to 10 carbon atoms.

16. A compound of formula (II):

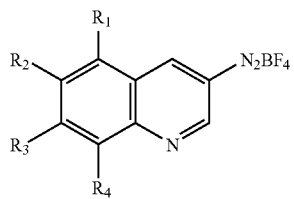

wherein $R_1$, $R_2$, $R_3$ and $R_4$ which may be identical or different, represent:
  a hydrogen atom;
  a fluorine atom;
  a linear, branched or cyclic alkyl radical optionally substituted with one to three fluorine atoms, with a group $OR_5$ in which $R_5$ represents a linear or branched alkyl radical, a hydrogen atom or a hydroxyl radical-protecting group, or with a group NR'R" in which R' and R", which may identical or different, represent a linear or branched alkyl radical, a hydrogen atom or an amino radical-protecting group;
  a group $OR_6$ in which $R_6$ represents a hydrogen atom, a phenol-protecting group or a linear or branched alkyl radical optionally substituted with one to three fluorine atoms, with $OR_5$ or with NR'R" as defined above;
  a group $NR'_1R"_1$ in which $R'_1$ and $R"_1$ have the values of R' and R" or represent a linear or branched alkyl radical substituted with one to three fluorine atoms, with a group $OR_5$ as defined above or with a group NR'R" as defined above;
  a group $CO_2R_a$, in which $R_a$ represents a hydrogen atom, a linear or branched alkyl radical or a carboxyl radical-protecting group;
a phenyl radical or a heteroaryl radical, optionally substituted with one or more of the substituents mentioned above.

* * * * *